(12) United States Patent
Kim et al.

(10) Patent No.: US 7,271,890 B2
(45) Date of Patent: Sep. 18, 2007

(54) METHOD AND APPARATUS FOR INSPECTING DEFECTS

(75) Inventors: Joung-Soo Kim, Gyeonggi-do (KR);
Yu-Sin Yang, Seoul (KR);
Moon-Kyung Kim, Gyeonggi-do (KR);
Sang-Mun Chon, Gyeonggi-do (KR);
Sun-Yong Choi, Gyeonggi-do (KR);
Chung-Sam Jun, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 346 days.

(21) Appl. No.: 10/903,852

(22) Filed: Jul. 30, 2004

(65) Prior Publication Data

US 2005/0094137 A1 May 5, 2005

(30) Foreign Application Priority Data

Aug. 1, 2003 (KR) ............... 10-2003-0053537

(51) Int. Cl.
*G01N 21/00* (2006.01)
(52) U.S. Cl. ............... 356/237.2; 356/237.4; 356/237.5
(58) Field of Classification Search ............... None
See application file for complete search history.

(56) References Cited

U.S. PATENT DOCUMENTS 4,902,131 A * 2/1990 Yamazaki et al. .......... 356/336
5,105,092 A * 4/1992 Natsubori et al. .......... 250/559.06
6,496,256 B1 12/2002 Eytan et al.
6,833,913 B1 * 12/2004 Wolf et al. ............... 356/237.2

FOREIGN PATENT DOCUMENTS

| JP | 06-249791 | 9/1994 |
|---|---|---|
| KR | 1988-0000750 | 12/1983 |
| KR | 1020020030674 | 4/2002 |

OTHER PUBLICATIONS

English language abstract of Korean Publication No. 1988-0000750.
English language abstract of Korean Publication No. 1020020030674.
English language abstract of Japanese Publication No. 06-249791, Sep. 9, 1994.

* cited by examiner

*Primary Examiner*—Michael P. Stafira
(74) *Attorney, Agent, or Firm*—Marger Johnson & McCollom, P.C.

(57) ABSTRACT

In a method for inspecting a defect in accordance with one aspect of the present invention, an object is divided into a plurality of regions. Reflectivity of each of the plurality of regions is obtained. Amplification ratio for each region is determined using the reflectivity. A light is irradiated onto the regions. A light reflected from a first region is amplified by a first amplification ratio that is determined for the first region. Moving the irradiated light from the first region to a second region is detected. A light reflected from the second region is amplified by a second amplification ratio that is determined for the second region. The amplified lights from the first region and the second region are analyzed to determine an existence of a defect on the object.

19 Claims, 4 Drawing Sheets

METHOD AND APPARATUS FOR INSPECTING DEFECTS

CROSS REFERENCE TO RELATED APPLICATION

This application claims priority under 35 USC § 119 to Korean Patent Application No. 2003-53537, filed on Aug. 1, 2003, the content of which is herein incorporated by reference in its entirety for all purposes.

BACKGROUND OF THE INVENTION

1. Field of the Invention

The present invention relates to a method and an apparatus for inspecting defects. More particularly, the present invention relates to a method and an apparatus for conducting a rapid and accurate inspection of a defect, for example, a particle and/or a scratch that exists on a semiconductor substrate.

2. Description of the Related Arts

To process massive data in a short time, a semiconductor device has been highly integrated. To manufacture the highly-integrated semiconductor device, a method of precisely depositing a thin film pattern on a semiconductor substrate is very important. Accordingly, an inspection process for determining a failure of the thin film pattern on the substrate is required. For example, after a patterning process for forming a minute pattern is performed, a defect such as a particle or a minute scratch may be generated thereon. Also, after a chemical mechanical polishing (CMP) process is performed on the substrate, the defect may be generated.

A conventional inspection apparatus only detects the presence of the defect on an object. The substrate having the defect is re-inspected by an inspector. The inspector inspects the substrate using a review tool and the inspector's naked eye.

As the semiconductor device is highly integrated, however, the defects uncovered by inspection on a single substrate have remarkably increased. Where tens of inspection defects have been uncovered in the past on the single substrate, hundreds or thousands of defects are found by inspection on a single substrate today.

Although the numbers of defects have remarkably increased as mentioned-above, the inspection apparatus has been slowly developed so that inspection time has also greatly increased. This decreases the productivity of the semiconductor devices.

A plurality of minute structures can be formed on a substrate. When these minute structures are inspected using available technology, the productivity of the semiconductor device decreases.

To prevent this decrease of the productivity, only selected substrates are inspected. Thus, an arbitrary substrate is selected from the entire production of substrates for inspection purposes. The selected substrate is only inspected to determine failures of the entire substrate. However, even though the inspection time is curtailed, the reliability of the inspection process is reduced contrarily.

Figure 1:
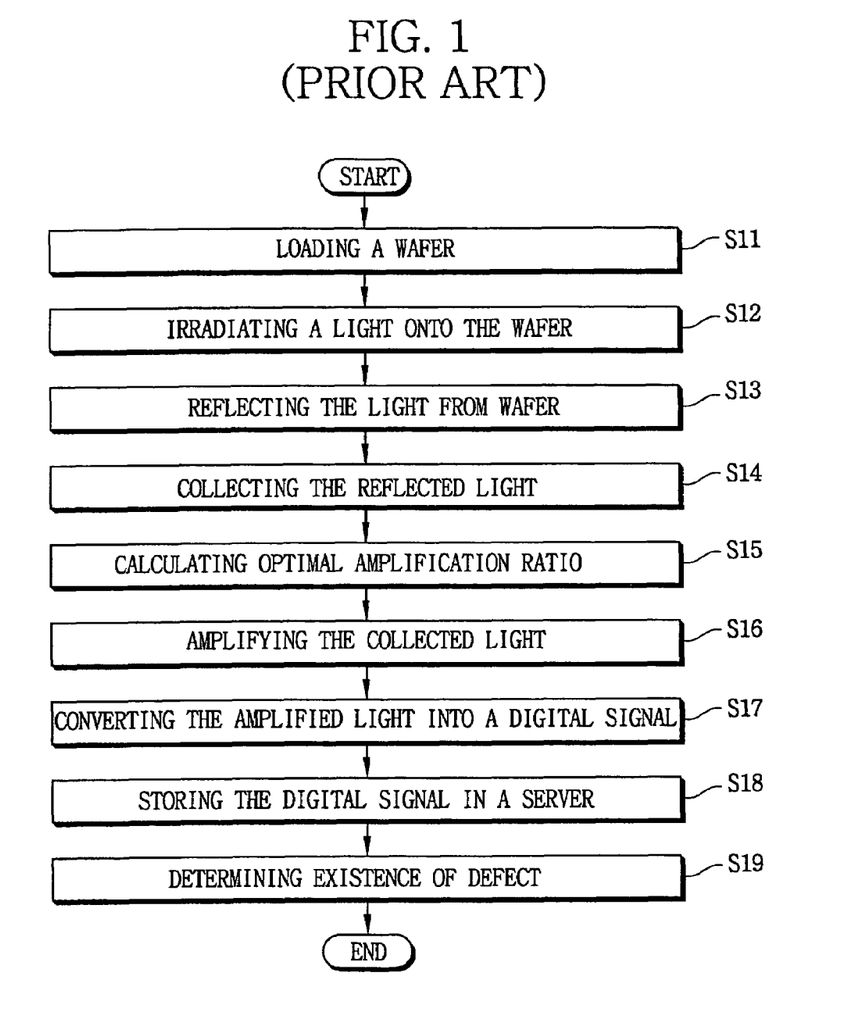
FIG. 1 is a flow chart illustrating a conventional method for inspecting a defect.

Referring to FIG. 1, in step S11, an arbitrarily selected wafer is loaded into an inspection apparatus. In step S12, a light is irradiated onto the wafer. In step S13, the irradiated light is reflected from the wafer. In step S14, the reflected light is collected using a photomultiplier tube. In step S15, the photomultiplier tube is employed to calculate an optimal amplification ratio in accordance with the intensity of the collected light. In step S16, the photomultiplier tube amplifies the collected light in accordance with the amplification ratio. In step S17, the amplified light is converted into a digital signal. In step S18, the digital signal is stored in a server. In step S19, the digital signal is compared to stored predetermined information for a reference wafer to determine the presence of a defect on the selected wafer.

Meanwhile, a plurality of minute structures, for example a line, a space, a contact hole or a pattern, is formed on a wafer. The minute structures may be divided into a cell region, a peripheral region and a sense amplifier.

Generally, these regions are repeatedly arrayed on the wafer. The minute structures formed in a same region have a substantially equal reflectivity. However, the minute structures formed in different regions have a different reflectivity. Thus, when a substantially the same light is irradiated on the different regions, the reflected lights may have a different reflectivity.

Further, when the reflected lights having the different reflectivities are amplified by the same amplification ratio, image information in at least one region may result in failure.

In particular, the reflected lights are collected using the photomultiplier tube. The photomultiplier tube generates photoelectrons in accordance with intensities of the collected lights. The photoelectrons create photoelectric currents having different intensities in accordance with the number of the photoelectrons present. Since the irradiated lights have a relatively low intensity, amplifying the irradiated lights is required. Accordingly, the irradiated lights are amplified differently in accordance with the voltage of the photomultiplier tube. As a result, a high photoelectric current is obtained from the irradiated light having a low intensity by controlling the voltage of the photomultiplier tube.

The photoelectric current is converted into a digital signal. The digital signal includes the image information of the minute structure on which the light is irradiated. Thus, the shape of the minute structure may be determined by analyzing the digital signal. When the voltage of the photomultiplier tube is constant, the collected light is amplified by a substantially equal amplification ratio. However, since the minute structures have different reflectivity levels, the collected lights are converted into the digital signal having clear image information from amplifying the collected light by different amplification ratios. Namely, when the voltage of the photomultiplier tube is not desirably controlled, the minute structure having a high reflectivity is shown in relatively high bright image, while the minute structure having a low reflectivity is shown in relatively low dark image. As a result, the shape of the minute structures may not be accurately determined.

As described above, the minute structures positioned in a same region have an equal or a similar reflectivity. When the light scans from one region to another region on the wafer, the amplification ratio of the photomultiplier tube typically varies.

When the number of the defects on the wafer exceeds a predetermined number after primarily inspecting the wafer using the photomultiplier tube, equipment for manufacturing a semiconductor device is suspended. The wafer having excessive defects is reviewed using a review tool. Here, the shapes of the defects are verified by the inspector's naked eye using the review tool.

Accordingly, performing the primary inspection accurately using the photomultiplier tube is required. Since reviewing the wafer using the inspector's naked eye in a secondary inspection is restricted by the quality of sight of the inspector, error in the primary inspection needs to be reduced as much as possible. Further, when the defects are not precisely inspected in the primary inspection, the wafer having the defects may be transferred to a subsequent process line.

As mentioned above, reviewing the wafer using the inspector's naked eye is determined in accordance with result of the primary inspection using the photomultiplier tube. Entire processes are then determined based on this reviewing result. When the review is carried out based on inaccurate result of the primary inspection, unnecessary time loss may be induced and also the defects may not be accurately inspected.

Figure 2:
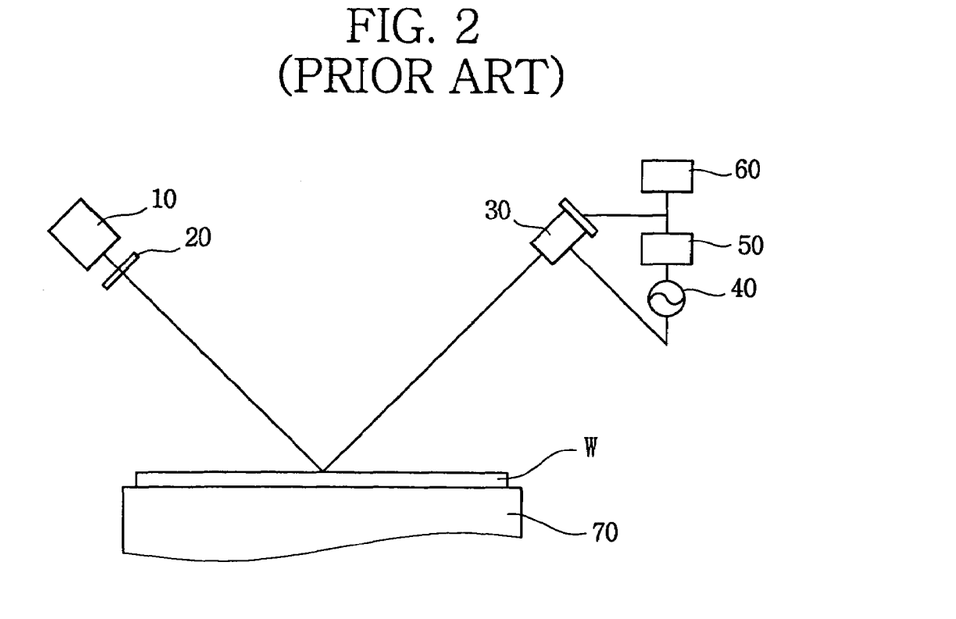
FIG. 2 is a front view illustrating a conventional apparatus for inspecting a defect.

Referring to FIG. 2, a conventional apparatus for inspecting a defect includes a light source 10 for irradiating a light onto a wafer W, a polarizer 20 for polarizing the irradiated light, a photomultiplier tube 30 for collecting light reflected from the wafer W, a power source 40 for providing current to the photomultiplier tube 30, a controller 50 for controlling a predetermined amplification ratio of the photomultiplier tube 30, and a central processor 60 for determining defects on the wafer W using the reflected light.

The wafer is disposed on a stage 70. The stage 70 is provided at a center of the inspection apparatus. The light source 10 is inclined at an angle of about 45° from the stage 70. The polarizer 20 is disposed between the light source 10 and the stage 70. The photomultiplier tube 30 is disposed at a position to readily collect the reflected light. An analog/digital (A/D) converter (not shown) is provided in the central processor 60. The A/D converter converts the reflected light into a digital signal stored in a server (not shown).

An operation algorithm of the photomultiplier tube 30 may be classified into a fixed gain type algorithm and an adaptive gain type algorithm. The fixed gain type algorithm is operated in accordance with a constant amplification ratio regardless of an amount and an intensity of the irradiated light. Since the amplification ratio of the photomultiplier tube 30 does not vary at the boundary at which the intensity of the irradiated light is changed, the image of an object such as the wafer W is light saturated.

The saturation of the image is illustrated in detail. The entire light reflected from the wafer W is amplified by substantially the same amplification ratio regardless of the intensity of the reflectivity varied in the fixed gain type algorithm. When output signals of the light reflected from one region of the wafer W having a high reflectivity, and from another region of the wafer W having a low reflectivity, are not amplified with different amplification ratios, the output signal of the light reflected from the region having the high reflectivity is higher than that of the light reflected from the region having the low reflectivity. Accordingly, the minute structure on the region having the low reflectivity is shown as a dim image.

The adaptive gain type algorithm is operated in accordance with different amplification ratios that vary according to an amount and an intensity of the irradiated light. That is, the amplification ratio of the light reflected from the high reflective region decreases, whereas that of the light reflected from the low reflective region increases. Thus, a dark region and a bright region are clearly distinguished in the adaptive gain type algorithm. As a result, the adaptive gain type algorithm has excellent inspection performance compared to that of the fixed gain type algorithm.

However, since a delay time occurs in the adaptive gain type algorithm, the saturation of the image is partially shown in the adaptive gain type algorithm. In particular, when the irradiated light is moved from the low reflective region, such as the cell region, to the high reflective region, such as the peripheral region or the sense amplifier, the delay time for sensing the moving light and for determining an optimal amplification ratio by the controller is required. The saturation of the image occurs using the adaptive gain type algorithm due to the delay time. As a result, the inspection performance of the conventional apparatus may be reduced.

Therefore, the saturation of the image deteriorates the performance of the inspection apparatus. When the defects are determined to be abnormal in accordance with information collected with the photomultiplier tube 30 in the delay time, the unnecessary reviewing of the wafer may be carried out. Further, since reviewing the wafer is performed through the inspector's manual operation, the time for reviewing the wafer is substantially longer than that required in using the automatic inspection apparatus.

SUMMARY OF THE INVENTION

The present invention provides a method for inspecting a defect, which is capable of accurately detecting a defect on an object by calculating optimal amplification ratios of each region and by preventing an image of the object from saturating, and capable of reducing a time for reviewing the object.

The present invention also provides an apparatus for inspecting a defect, which is capable of detecting a defect rapidly and precisely on an object by minimizing a saturation of an object image.

In a method for inspecting a defect in accordance with one aspect of the present invention, an object is divided into a plurality of regions. Reflectivity of each of the plurality of regions is obtained. Amplification ratio for each region using corresponding reflectivity is defined. A light is irradiated onto the regions. A light reflected from a first region is amplified by a first amplification ratio that corresponds to the first region. Moving the irradiated light from the first region to a second region is detected. A light reflected from the second region is amplified by a second amplification ratio corresponding to the second region. The amplified lights from the first region and the second region are analyzed to determine an existence of a defect on the object.

An apparatus for inspecting a defect in accordance with another aspect of the present invention includes a stage on which an object is disposed. An emitter irradiates a light onto regions of the object. A detector collects a light reflected from the object, and amplifies the collected light by an amplification ratio. A controller changes the amplification ratio in accordance with a reflectivity that corresponds to any one of the regions. A determiner determines an existence of a defect on the object by analyzing the amplified light.

According to the present invention, since the optimal amplification ratios of the regions are determined in advance, the saturation of the object image is prevented. Therefore, the entire defects on the object are accurately inspected. Further, unnecessary reviewing of the object is also prevented.

BRIEF DESCRIPTION OF THE DRAWINGS

The above objects and advantages of the present invention will become more apparent by describing preferred embodiments in detail with reference to the attached drawings in which.

DESCRIPTION OF THE PREFERRED EMBODIMENT

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this closure will be thorough and complete, and will fully convey the scope of the invention to those skilled persons in the art.

Hereinafter, a method and an apparatus for inspecting a defect in accordance with one embodiment of the present invention are illustrated in detail.

Figure 3:
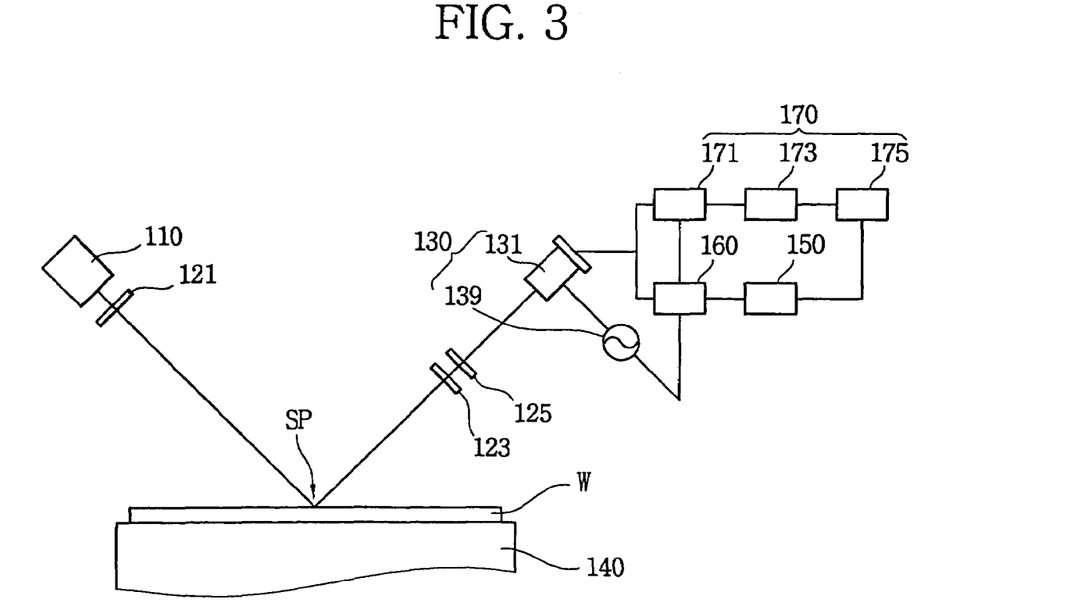
FIG. 3 is a front view illustrating an apparatus for inspecting a defect in accordance with one embodiment of the present invention.
Figure 4:
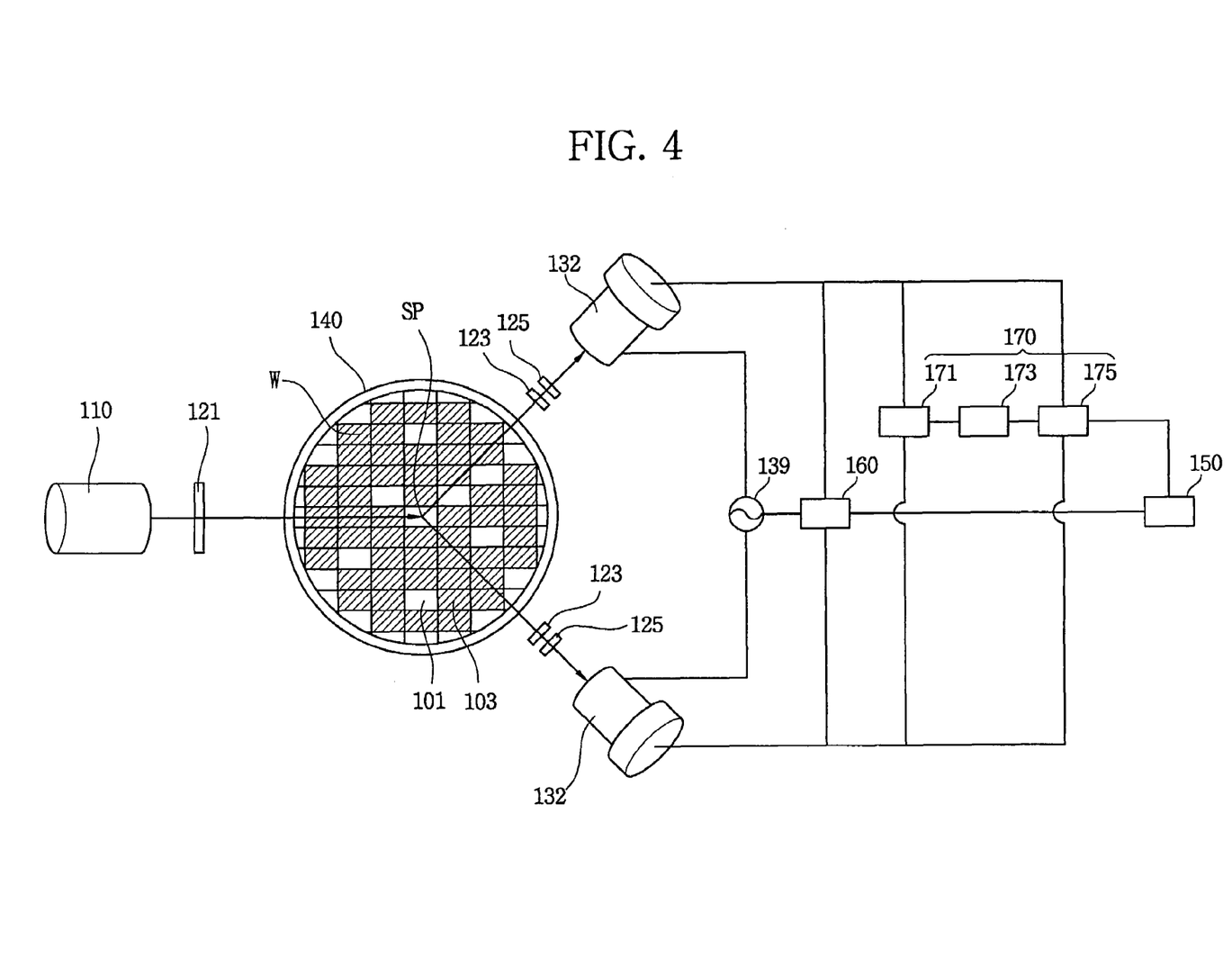
FIG. 4 is a plan view illustrating the apparatus for inspecting a defect in FIG. 3.

Referring to FIG. 3, an apparatus for inspecting a defect includes a stage 140 on which a wafer W is disposed. Here, a surface of the wafer W is divided into regions. An emitter 110 irradiates a light onto regions of the wafer W. A detector 130 collects light reflected from the wafer W. The detector 130 also amplifies the collected light by a predetermined amplification ratio. Reflectivity of the each region is stored in a memory 150. A controller 160 receives the reflectivity reading from each region, and then varies the amplification ratio of the collected light in accordance with the reflectivity of each region. A determiner 170 analyzes the amplified light so as to ascertain the existence of a defect on the wafer W.

The determiner 170 includes an AID converter 171 for converting the amplified light into a digital signal, an image processor 173 for converting the digital signal into image information, and a calculator 175 for calculating a signal difference between the converted image and a predetermined reference image. This calculation is accomplished by comparing the images with each other and thereby determining the existence of the defect on the region.

The wafer W is supported on the stage 140. The wafer W on the stage 140 is moved in a horizontal direction. Thus, the light can be irradiated on the entire surface of the wafer W as it is horizontally moved with respect to the stage 140.

The emitter 110 irradiates the light on the wafer W. The emitter 110 irradiates the light in a direction substantially perpendicular to or inclined with respect to the surface of the wafer W. The emitter 110 is preferably disposed at an angle of about 20° with respect to the surface of the wafer W to irradiate the light at an angle with respect to the surface of the wafer W. Preferably, the emitter 110 may be disposed at an angle of from about 10° to about 90° with respect to the surface of the wafer W. The inclined angle of the emitter 110 may be adjusted in accordance with the inspection apparatus or inspection processes.

The light preferably includes a laser that has a predetermined wavelength or wavelength range. Preferably, the laser has a wavelength of about 48 nm which is the most stable for inspecting the wafer for defects.

A first polarizer 121 is disposed between the wafer W and the emitter 110. A second polarizer 123 is disposed between the wafer W and the detector 130. A condenser 125 is disposed between the second polarizer 123 and the detector 130. The first polarizer 121 includes a polarizing plate. For example, the plate can have a ½ wavelength or a ¼ wavelength.

Accordingly, the light emitted from the emitter 110 is converted into a polarized light, such as a primary (P) polarized light, a secondary (S) polarized light or a circular (C) polarized light. Since the defect on the wafer W is readily detected using the polarized light, the polarized light is irradiated on the wafer W. In particular, the irradiated light is reflected in a different manner from the defect on the wafer W in accordance with type of the polarized light employed. Thus, the polarized light is preferably irradiated on the wafer W for detecting the defect, and more specifically for simultaneously recognizing certain characteristics of the defect.

The polarizing plate for converting the irradiated light into the P polarized light, S polarized light or C polarized light is employed in one embodiment of the present invention. Alternatively, other polarizing plates capable for converting the irradiated light into a combined polarized light, for example, a P-S polarized light or S-C polarized light, may be employed in the inspection apparatus of the present invention. Thus, the polarizing plate may be selectively and readily changed depending on the circumstances of use in the detection process.

A light-path changing member (not shown) may be disposed between the emitter 110 and the wafer W. The light-path changing member may include mirrors. Thus, the light emitted from the emitter 110 may be irradiated onto the wafer W at various angles by the mirrors.

The polarized light generated through the first polarized member 121 defines an inspection spot SP on the wafer W. The inspection spot SP is a region of the wafer on which the polarized light is irradiated.

The polarized light is reflected from the inspection spot SP. Here, the polarized light may be totally reflected at an angle substantially identical to an incident angle of the polarized light, or may be scattered due to the defect on the inspection spot SP. The reflected light including the totally reflected light and the scattered light is collected in the detector 130.

A typical inspection apparatus inspects the defect using scattered light. However, it is not necessary to use the scattered light for detecting the defect. For example, when a minute structure formed on the wafer W does not have a defect, a majority of the incident lights may be totally reflected. On the contrary, when the minute structure has the defect, the majority of the incident lights may be scattered. Thus, when the totally reflected light is generated to a greater extent than the scattered light, the minute structure may be determined to be normal because the defect does not exist on the minute structure. On the contrary, when the scattered light is generated much more than the totally reflected light, the minute structure may be determined to be abnormal because the defect exists on the minute structure. Thus, the existence of a defect on the minute structure may be determined using either totally reflected light or scattered light. The light reflected from the wafer W is collected in the detector 130. The detector 130 includes photomultiplier tubes 131 and 132 for amplifying the collected light, and a power supply 139 for applying a voltage to the photomultiplier tubes 131 and 132.

The photomultiplier tubes 131 and 132 are positioned to readily collect the reflected light. The angle of the detector 130 with respect to the surface of the wafer W may be adjusted to various angles.

In particular, the photomultiplier tubes 131 and 132 may be disposed at an angle of from about ±40° to about ±50° with respect to the inspection spot SP. Preferably, the photomultiplier tubes 131 and 132 are disposed at an angle of about ±45° with respect to the inspection spot SP.

Here, the photomultiplier tubes 131 and 132 are a vacuum tube type light-receiving apparatus that varies an amplification ratio of the collected light in accordance with a high voltage. The photomultiplier tubes 131 and 132 may detect and measure a single photon, and also may be utilized within a wavelength of about 0.2 µm to about 1.1 µm. Further, the photomultiplier tubes 131 and 132 measure a dark current of about 0.3 pA (pico-ampere). The amplification ratio may be reached to hundreds times original amplitude by the photomultiplier tubes 131 and 132. Thus, the photomultiplier tubes 131 and 132 are preferable for measuring the light reflected from the surface of the wafer W.

The reflected light is filtered through the second polarizing member 123 to be changed into the polarized light having a specific wavelength. The filtered light may be the P polarized light, the S polarized light or the C polarized light. When any one of the P polarized light, the S polarized light and the C polarized light is used, a regular signal generated from the wafer is minimized, thereby distinguishing a signal generated from the defect, from the regular signal. The filtered light is concentrated on the photomultiplier tubes 131 and 132 through the condenser 125. The polarized light concentrated on the photomultiplier tubes 131 and 132 is amplified by a predetermined amplification ratio in accordance with the high voltage provided to the photomultiplier tubes 131 and 132.

The photomultiplier tubes 131 and 132 include a cathode for discharging a photoelectron when the light is irradiated, and an anode for collecting the discharged photoelectron. When a potential difference between the cathode and the anode is generated by providing a current to the anode, a photoelectric current flows from the cathode to the anode. The photoelectric current is proportional to the numbers of the photoelectron. The numbers of the photoelectron is also proportional to an intensity of the light that is applied to the cathode. Thus, the intensity of the light is obtained by measuring the photoelectric current.

When the intensity of the light is relatively low, dynode electrodes (not shown) are used in the photomultiplier tubes 131 and 132. The dynode electrodes are disposed between the anode and the cathode. The dynode electrodes generate a high potential difference between the cathode and the anode to increase energy of the photoelectron. The energy of the photoelectron is amplified corresponding to a voltage applied to a dynode electrode. That is, when high voltage is applied to the photomultiplier tubes 131 and 132, the high voltage is also applied to the dynode electrode so that the amplification ratio of the photoelectron greatly increases.

As described above, the photomultiplier tubes 131 and 132 output different photoelectric currents in accordance with the intensity of the light collected in the photomultiplier tubes 131 and 132. A photoelectric current having a low intensity is not directly used. Thus, the amplification ratio may be adjusted by controlling the voltage applied to the dynode electrodes disposed between the photomultiplier tubes 131 and 132.

Meanwhile, when substantially identical lights are irradiated to the wafer W, the intensities of the reflected lights are different in accordance with the reflectivity of the regions on the wafer W. Accordingly, it is desirable to amplify the reflected lights by the optimal amplification ratios that correspond to the respective regions. Particularly, the intensity of the light reflected from the high-reflective region, such as the cell region, is different from that of the light reflected from the low-reflective region, such as the sense amplifier or the peripheral region. The intensity difference between the respective lights is caused from differing kinds and intervals of the minute structures that are formed on each region. Thus, when the substantially identical lights are irradiated on each region, the intensities of the lights reflected from each region are different from each other.

The controller 160 is connected to the power supply 139 of the photomultiplier tubes 131 and 132. The controller 160 receives the optimal amplification ratios corresponding to each region, respectively, from the memory 150. The controller 160 controls the power supply 139 in accordance with the optimal amplification ratios to adjust the amplification ratios of the photomultiplier tubes 131 and 132.

The reflectivity of each region is stored in the memory 150. Information of each region is also stored in the memory 150. The optimal amplification ratios are obtained in a recipe setup process before the inspection process. The minute structures on the wafer W are divided into the regions. The light is irradiated on each region to obtain the reflectivity of each region. The optimal amplification ratio of the each region is determined in accordance with the reflectivity of each region.

The light emitted from the emitter 110 is changed into the polarized light through the first polarizing member 121. The polarized light is irradiated onto the wafer W. Since the wafer W disposed on the stage 140 is moved in the horizontal direction, the polarized light is subsequently irradiated onto at least two regions. The light reflected from the wafer W is filtered through the second polarizing member 123. The filtered light is concentrated on the photomultiplier tubes 131 and 132 through the condenser 125. Since the light is irradiated onto at least two regions, the reflected light concentrated on the photomultiplier tubes 131 and 132 has at least two intensity values. The reflected lights are amplified by the amplification ratios corresponding to the reflectivity of each region to prevent the images of the regions from being saturated.

The amplification ratio corresponding to each region is previously determined by irradiating the light onto the wafer W. Since a region on which the light is initially irradiated is recognized in advance, the amplification ratio of the region irradiated by the light thereon is also previously set. Alternatively, the amplification ratio of the region may not be set in an adaptive gain type operation algorithm that determines the amplification ratio in accordance with the intensity of the collected light. Accordingly, the light is initially irradiated onto the wafer to obtain the amplification ratio of the region using the adaptive gain type operation algorithm.

The reflected light is collected in the detector 130. The collected light is amplified in accordance with the predetermined amplification ratio. The amplified light is converted into a digital signal by the A/D converter 171. The digital signal is converted into the image information by the image processor 173. The image information is then provided to the calculator 175. The calculator 175 calculates a signal difference between the converted image and a predetermined reference image by comparing the images with each other. The calculator 175 then determines if there is a defect on the region.

When the wafer W on the stage 140 is horizontally moved, the light is irradiated onto another region. The intensity of the light reflected from another region differs from that of the light reflected from the above region. The intensity of the light varies at an interface between the regions.

The controller 160 senses variation of the intensity. The controller 160 receives the reflectivity of another region corresponding to the variation of the intensity from the memory 150. The controller 160 varies the amplification ratio of the photomultiplier tubes 131 and 132 in accordance with the reflectivity which is received. The controller 160 previously determines the amplification ratio of another region before the light is irradiated from one region to another region so that the light irradiated onto another region is amplified by the optimal amplification ratio. When the light is irradiated from one region to another region, the amplification ratio is previously adjusted using the light reflected from the interface.

Here, the surface of the wafer on which processes for manufacturing a semiconductor device are carried out may be divided into a cell region, a peripheral region, a sense amplifier and a sub-word divider. The regions having a substantially identical structure and are repeatedly arrayed on the surface of the wafer. Accordingly, when information relating to the light reflected from the interface between the adjacent regions is defined and then is stored, the time for obtaining the optimal amplification ratios of each region may be reduced.

The apparatus for inspecting a defect in accordance with one embodiment of the present invention determines the optimal amplification ratios of each region using a variation of the light reflected from the interface between the regions. However, the light reflected from the interface is not necessarily used in the inspection apparatus of the present invention. In particular, a path of the light is determined in accordance with a predetermined job profile in a typical inspection process. Thus, the optimal amplification ratios of coordinates on the wafer are defined such that the reflected light is amplified in accordance with the optimal amplification ratio corresponding to each coordinate.

However, since the regions having a substantially identical structure to each other are repeatedly arrayed on the typical wafer, determining the amplification ratio corresponding to each coordinate may be unnecessary. That is, the optimal amplification ratio corresponding to each region is obtained and then is used for each region, thereby reducing the inspection time. The optimal amplification ratio corresponding to each coordinate may be used in the inspection apparatus of the present invention.

Further, various optimal amplification ratios corresponding to each region that is set in the recipe setup process may be used in the inspection apparatus of the present invention. In particular, although wafers are manufactured using the same equipment, the characteristics of the wafers may be different. The results of the continuous inspection processes are stored in the memory 150 so that the characteristics of the wafers may be reflected on a successive inspection process. In the successive inspection process, the detector 130 receives the optimal amplification ratios from the memory 150 and simultaneously calculates the optimal amplification ratio of the collected light. Namely, although the detector 130 amplifies the reflected light in accordance with the received amplification ratios, and the detector 130 separately calculates the optimal amplification ratio of the collected light. The separately calculated amplification ratios are stored in the memory 150 to be used in the successive inspection process.

According to one embodiment of the present invention, the amplification ratios corresponding to each region on the wafer W are determined in advance and then are used in the inspection process so that time for calculating the optimal amplification ratios of corresponding regions by the detector 130 may be reduced. Therefore, the detector 130 inspects the minute structures on the wafer W without the saturation of the image. Additionally, since varying the minute structures at the interface between the regions is reflected on the inspection apparatus, the reflected light is amplified by the optimal amplification ratio in the inspection process.

The amplified light is converted into the digital signal through the A/D converter 171. The digital signal is converted into the image by the image processor 173. The calculator 175 aligns the center of the converted image with that of the reference image, and then calculates an offset between the images. The calculator 175 determines the defect of the region in accordance with the calculated offset.

When the numbers of the defects on the region exceed a reference number, the wafer is reviewed. Accordingly, the reflected light is amplified by the optimal amplification ratio in primary inspection process using the photomultiplier tubes 131 and 132 so that the saturation of the image is prevented. As a result, the defects on the wafer W are accurately inspected and classified, thereby reducing time for reviewing the wafer.

Figure 5:
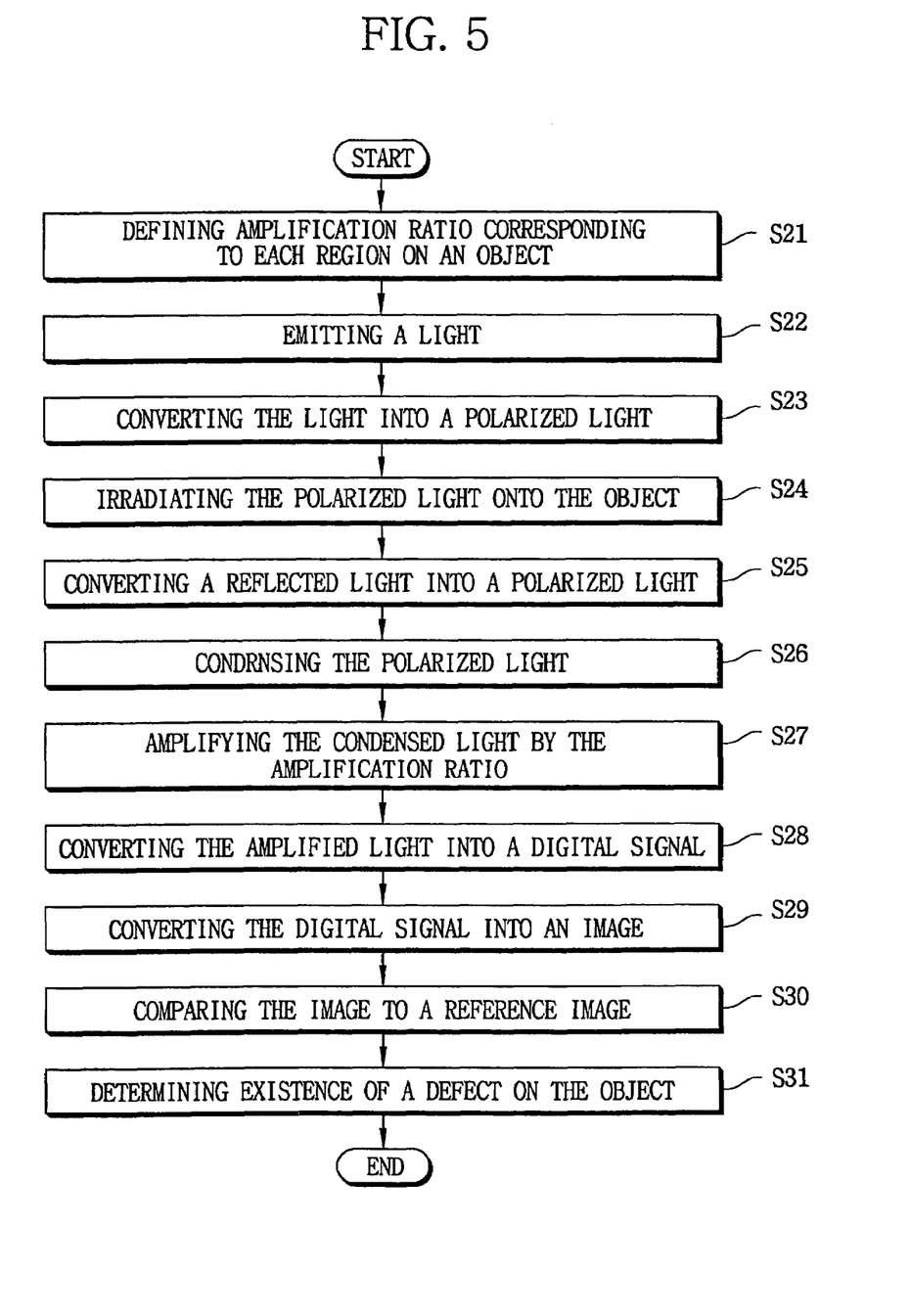
FIG. 5 is a flow chart illustrating a method for inspecting a defect in accordance with one embodiment of the present invention.

Referring to FIG. 5, in step S21, amplification ratios corresponding to each region on an object such as a wafer are determined.

In step S22, a laser having a wavelength of about 488 nm is emitted from an emitter. Alternatively, any other laser having a different wavelength from above mentioned wavelength may be used as the light. That is, a laser used for determining defects on the wafer is available in the present method.

The emitter is disposed at an angle of about 20° with respect to the surface of the wafer to slantingly irradiate the light at an angle of about 20° with respect to the surface of the wafer. Alternatively, the emitter 110 may be disposed at an angle of about 10° to about 90° with respect to the surface of the wafer. The emitters are disposed around the wafer to irradiate the light at various angles. The incident angles and the numbers of the lights are selected in accordance with kinds and conditions of the object.

In step S23, the emitted light is converted into a polarized light by passing through a first polarizer. The first polarizer is disposed between the wafer and the emitter. The first polarizer includes a polarizing plate having a ½ wavelength or a ¼ wavelength can be employed for this purpose. Accordingly, the light emitted from the emitter is converted into a polarized light such as a P polarized light, an S polarized light or a C polarized light. Since the defect on the wafer is readily detected using the polarized light, the polarized light is irradiated on the wafer. In particular, the irradiated light is reflected differently from the defect on the wafer in accordance with the kind of the polarized light employed. Thus, the polarized light is preferably irradiated on the wafer for detecting the defect and for simultaneously recognizing the characteristic of the defect.

The polarizing plate for converting the irradiated light into the P polarized light, the S polarized light or the C polarized light is employed in one embodiment of the present invention. Alternatively, other polarizing plate capable of converting the irradiated light into a combined polarized light, for example a P-S polarized light or S-C polarized light, may be employed in the inspection apparatus of the present invention. That is, the polarizing plate may be selectively and readily changed into other ones by persons skilled in the art.

In step S24, the wafer is horizontally moved to irradiate the light onto the entire surface of the wafer. Here, moving the emitter for irradiating the light onto the entire surface of the wafer is disadvantageous because a detector is moved together with the emitter. The polarized light may be totally reflected at an angle substantially identical to an incident angle of the polarized light or may be scattered due to the defect on the wafer.

The light reflected from the wafer is collected at various positions. The detector includes photomultiplier tubes preferably used for collecting the reflected light. The angle of the photomultiplier tubes with respect to the surface of the wafer W may be adjusted. The photomultiplier tubes may be preferably disposed at an angle of about ±45° with respect to the surface of the wafer.

In step S25, the reflected light is converted into a polarized light by passing it through a second polarizer. The second polarizer is disposed between the detector and the wafer.

In step S26, the polarized light is concentrated on the detector by passing it through a condenser. Thus, the concentrated light is the P polarized light, the S polarized light or the C polarized light. When any one of the P polarized light, the S polarized light and the C polarized light is used, a conventional signal generated from the wafer is minimized. Instead, a signal is generated from the defect which is distinguishable from the conventional signal.

The polarized light concentrated on the photomultiplier tubes is amplified by a predetermined amplification ratio in accordance with a high voltage provided to the photomultiplier tubes. The photomultiplier tubes generate a photoelectric current in accordance with the intensity of the collected light. Thus, the intensity of the light can be obtained by measuring the photoelectric current.

The photoelectric current having a low intensity is not directly used. Instead, the photoelectric current is amplified using the photomultiplier tubes.

Meanwhile, when substantially identical lights are irradiated onto the wafer W, the intensities of the reflected lights vary in accordance with the reflectivity of the regions on the wafer W which are irradiated. Accordingly, the reflected lights are amplified by the optimal amplification ratios that correspond to the respective regions. For example, the intensity of the light reflected from the high-reflective region, such as the cell region, is different from that of the light reflected from the low-reflective region, such as the sense amplifier or the peripheral region. The difference between the intensities of the respective lights is caused from differing kinds and intervals of the minute structures that are formed on each region. Thus, when the substantially identical lights are irradiated on each dissimilar region, the intensities of the lights reflected from the each region are different from each other. Accordingly, the reflected light is amplified by different ratios in accordance with the reflectivity of the each region. Additionally, information from each region as previously defined can be used in the inspection process.

Meanwhile, the amplification ratios corresponding to the each region are determined by irradiating the light onto the wafer W. Since a region on which the light is initially irradiated is recognized in advance, the amplification ratio of the region irradiated by the light thereon can also be established.

When the wafer is horizontally moved, the light is irradiated from one region to another region. The intensity of the light reflected from a region differs from that of the light reflected from another region. The intensity of the light varies at an interface between the regions.

In step S27, when the intensity of the reflected light varies at the interface, the amplification ratio is changed into another amplification ratio corresponding the corresponding intensity of the reflected light. The collected light is amplified in accordance with another amplification ratio.

That is, another amplification ratio is set before the light is irradiated from one region to another region, so that the light reflected another region is amplified by another amplification ratio. In particular, when the light is irradiated from one region to another region, the variation of the regions is recognized using the light reflected from the interface, thereby changing the amplification ratio.

Here, the surface of the wafer on which processes for manufacturing a semiconductor device are carried out may be divided into a cell region, a peripheral region, a sense amplifier and a sub-word divider. The regions having a substantially identical structure are repeatedly arrayed on the surface of the wafer. Accordingly, when information of the light reflected from the interface between the adjacent regions is defined and then is stored, the time for obtaining the optimal amplification ratios of each region may be reduced.

The method for inspecting a defect in accordance with one embodiment of the present invention determines the optimal amplification ratios of each region using the variation of the light reflected from the interface between the regions. However, the light reflected from the interface may not necessarily be used in the inspection method of the present invention. In particular, a path of the light is determined in accordance with a predetermined job profile in a typical inspection process. Thus, the optimal amplification ratios of coordinates on the wafer are determined such that the reflected light is amplified in accordance with the optimal amplification ratio corresponding to each coordinate.

However, since the regions having a substantially identical structure are repeatedly arrayed on the typical wafer, determining the amplification ratios corresponding to each coordinate may be unnecessary. That is, the optimal amplification ratio corresponding to each region is obtained and then is used for each region, thereby reducing the inspection time. The optimal amplification ratios corresponding to each coordinate may be used in the inspection method of the present invention.

Further, variable optimal amplification ratios corresponding to each region that is set in the recipe setup process may be used in the inspection method of the present invention. In particular, although wafers are manufactured using same equipment, characteristics of the wafers may be different. Results of the continuous inspection processes are stored so that the characteristics of the wafers may be reflected on a successive inspection process. In the successive inspection process, the reflected light is collected and simultaneously amplified by the optimal amplification ratio. Although the reflected light is amplified in accordance with the amplification ratio, the optimal amplification ratio of the separately collected light is calculated. The separately calculated amplification ratios are used in the successive inspection process.

Accordingly, the amplification ratios corresponding to each region on the wafer are determined in advance and then are used in the inspection process so that time for calculating the optimal amplification ratios of corresponding regions may be reduced. Therefore, the minute structures on the wafer are inspected without the saturation of the image. Additionally, since varying the minute structures at the interface between the regions is reflected on the inspection method, the reflected light is amplified by the optimal amplification ratio in the inspection process.

When the numbers of the defects on the region exceed a reference number, the wafer is reviewed. Accordingly, the reflected light is amplified by the optimal amplification ratio in primary inspection process using the photomultiplier tubes so that the saturation of the image is prevented. As a result, the defects on the wafer are accurately inspected and classified, thereby reducing time for reviewing the wafer.

According to the present invention, the optimal amplification ratios corresponding each region on the object are determined in advance so that the image of the object may not be saturated. Therefore, the defects on the object may be accurately inspected, thereby reducing time for reviewing the object.

Further, time for inspecting the wafer may be significantly reduced considering the numbers of the reviewed wafers in the semiconductor fabricating processes. As a result, reliable results of the inspection may be provided using the present invention so that great parts of the inspection apparatus may be automatically operated.

Having described the preferred embodiment, it is noted that modifications and variations can be made by persons skilled in the art in light of the above teachings. It is therefore to be understood that changes may be made in the particular embodiment of the present invention disclosed which is within the scope and the spirit of the invention outlined by the appended claims.

What is claimed is:

1. A computer-implemented method for inspecting an object for defects comprising:
    obtaining reflectivity of each of a plurality of regions on the object;
    determining an amplification ratio for each of the regions based on the reflectivity of each of the regions;
    irradiating a light onto the plurality of regions;
    amplifying a light reflected from a first region by a first amplification ratio that is determined for the first region;
    detecting whether the irradiated light has been transferred from the first region to a second region;
    amplifying a light reflected from the second region by a second amplification ratio that is determined for the second region;
    storing signals with respect to the first and second amplification ratios in a computer; and
    analyzing the amplified lights from the first region and the second region to determine the existence of a defect on the object.

2. The method of claim 1, wherein determining the existence of the defect comprises:
    converting the amplified light into a digital signal;
    converting the digital signal into an image;
    comparing the image to a predetermined reference image to obtain a difference between the images; and
    determining the existence of the defect on the region on which the light is irradiated based on the difference between the images.

3. The method of claim 1, wherein the object comprises a wafer, and the regions include at least one of a cell region, a peripheral region and a sense amplifier on the wafer.

4. The method of claim 1, further comprising polarizing the light prior to irradiating the light.

5. The method of claim 1, wherein the polarized light comprises at least one of a primary (P) polarized light, a secondary (S) polarized light and a circular (C) polarized light.

6. The method of claim 1, wherein the light is irradiated at an angle of from about 10° to about 90°.

7. The method of claim 1, further comprising:
    converting the reflected lights into polarized lights;
    condensing the polarized lights; and
    amplifying the condensed lights.

8. The method of claim 7, wherein the polarized lights comprises at least one of a P polarized light, an S polarized light and a C polarized light.

9. An apparatus for inspecting an object for a defect comprising:
    a stage for supporting and transferring the object;
    an emitter for irradiating a light onto a plurality of regions on the object;
    a detector for collecting a light reflected from the object and for amplifying the collected light by an amplification ratio;
    a first polarizer disposed between the emitter and the object, the first polarizer converting the light emitted from the emitter into a first polarized light;
    a second polarizer disposed between the object and the detector, the second polarizer converting the light reflected from the object into a second polarized light;
    a controller for changing the amplification ratio based on reflectivity that is determined for any one of the plurality regions; and
    a determiner for determining an existence of a defect on the object by analyzing the amplified light.

10. The apparatus of claim 9, wherein the first and second polarized lights comprise at least one of a P polarized light, an S polarized light and a C polarized light.

11. The apparatus of claim 9, wherein the light from the emitter is reflected from the object at an angle of about 10° to about 90° with respect to the object.

12. The apparatus of claim 9, wherein the detector comprises:
    a photomultiplier tube for collecting and amplifying the reflected light; and
    a power supply for supplying power to the photomultiplier tube, wherein the power is controlled based on the reflectivity.

13. The apparatus of claim 9, wherein the determiner comprises:
    an analog/digital converter for converting the amplified light into a digital signal;
    an image processor for converting the digital signal into an image; and
    a calculator for calculating a difference between the image and a reference image by comparing the both images with each other to determine the existence of the defect on the object.

14. The apparatus of claim 9, further comprising a memory in which the reflectivity and a determined result of the determiner are stored.

15. The method of claim 9, wherein the object comprises a wafer, and the regions include at least one of a cell region, a peripheral region and a sense amplifier on the wafer.

16. A computer-implemented method for inspecting an object for defects comprising:
    obtaining reflectivity of each of a plurality of regions on the object;

determining an amplification ratio for each of the regions based on the reflectivity of each of the regions;
irradiating a light onto the plurality of regions;
amplifying a light reflected from a first region by a first amplification ratio that is determined for the first region;
converting the amplified light into a digital signal;
detecting whether the irradiated light has been transferred from the first region to a second region;
amplifying a light reflected from the second region by a second amplification ratio that is determined for the second region;
converting the amplified light into a digital signal;
storing signals with respect to the first and second amplification ratios in a computer; and
analyzing the amplified lights from the first region and the second region to determine the existence of a defect on the object.

17. The method of claim 16, wherein determining the existence of the defect further comprises converting the digital signal into an image.

18. The method of claim 17, wherein determining the existence of the defect further comprises comparing the image to a predetermined reference image to obtain a difference between the images.

19. The method of claim 18, wherein determining the existence of the defect on the region on which the light is irradiated is based on the difference between the images.

* * * * *

UNITED STATES PATENT AND TRADEMARK OFFICE
CERTIFICATE OF CORRECTION

PATENT NO. : 7,271,890 B2  Page 1 of 1
APPLICATION NO. : 10/903852
DATED : September 18, 2007
INVENTOR(S) : Joung-Soo Kim et al.

It is certified that error appears in the above-identified patent and that said Letters Patent is hereby corrected as shown below:

Column 5, line 33, the words "of the each" should read -- of each --;
Column 5, line 39, the word "AID" should read -- A/D --.

Signed and Sealed this

Sixteenth Day of September, 2008

JON W. DUDAS
*Director of the United States Patent and Trademark Office*